United States Patent [19]

Champseix et al.

[11] 4,064,255
[45] Dec. 20, 1977

[54] COMPOSITIONS CONTAINING NEW INDOLE DERIVATIVES AND THEIR USE IN PHARMACOLOGY

[75] Inventors: Alain André Champseix, Forges les Bains Limours; Claude Georges Alexandre Gueremy, Houilles; Gerard Roger Le Fur, Villeneuve la Garenne, all of France

[73] Assignee: Mar-Pha Societe d'Etudes et d'Exploitation de Marques, Paris, France

[21] Appl. No.: 679,970

[22] Filed: Apr. 26, 1976

[30] Foreign Application Priority Data

Dec. 12, 1975 France .................. 75.38051

[51] Int. Cl.² ............................................ A61K 31/445
[52] U.S. Cl. .................................................... 424/267
[58] Field of Search .................... 424/267; 260/293.61

[56] References Cited

U.S. PATENT DOCUMENTS

| | | | |
|---|---|---|---|
| 3,136,770 | 6/1964 | Gray | 260/293.61 |
| 3,287,461 | 11/1966 | Gray | 260/293.61 |
| 3,644,403 | 2/1972 | Canas-Rodriguez et al. | 260/293.61 |
| 3,946,029 | 3/1976 | Descamps | 260/293.61 |

FOREIGN PATENT DOCUMENTS

| | | |
|---|---|---|
| 1,693M | 3/1961 | France. |
| 1,126,245 | 9/1968 | United Kingdom. |

*Primary Examiner*—Stanley J. Friedman
*Attorney, Agent, or Firm*—Beveridge, Degrandi, Kline & Lunsford

[57] ABSTRACT

Compositions containing indole derivatives of the formula

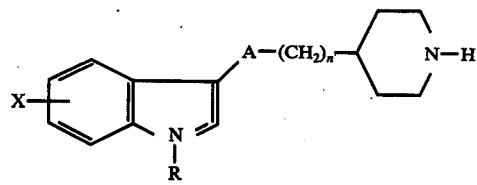

are useful in pharmacology.

33 Claims, No Drawings

COMPOSITIONS CONTAINING NEW INDOLE DERIVATIVES AND THEIR USE IN PHARMACOLOGY

The present invention relates to new compositions containing derivatives of indole which compositions are useful in the treatment of pathological conditions caused by disturbances in the serotonin systems. In particular, these compounds may be used as psychotropic drugs, and in particular as anti-depressants in mammels.

They may be represented by the formula

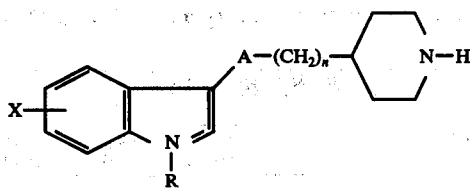

(I)

wherein R is a hydrogen atom, an alkyl group having from 1 to 4 carbon atoms, or an aralkyl group of which the alkyl has 1 or 2 carbon atoms, X is a hydrogen atom, alkyl, alkoxy or alkylthio containing from 1 to 4 carbon atoms, a halogen atom such as chlorine, fluorine, bromine, a trifluoromethyl, nitro, hydroxy or amino group, the latter possibly being substituted by one or two alkyl groups, by an acyl group or by an alkyl-sulfonyl group; and A represents —CO— or —CH$_2$— group and n has the values 0, 1 and 2.

A certain number of compounds of formula (I) already are known (J. I. de Graw, J. Heterocyclic Chemistry 1966, 3 (I), pages 67–69, French Pat. No. 1693 M, British Pat. No. 1,126,245). Some have been used as intermediary products to prepare derivatives with analgesic properties, but none so far has been proposed as a drug.

Coming within the scope of formula I above are compounds wherein A is the —CO— group in which instance the compounds are ketones. These compounds are illustrated in examples 1 to 7.

Also coming within the scope of formula I above are compounds wherein A is the hydrocarbon group —CH$_2$— and this group of compounds is illustrated by examples 8 to 14.

Still further coming within the scope of formula I above are compounds wherein A is —CO— or —CH$_2$— and R is hydrogen, alkyl from 1 to 4 or aralkyl wherein the alkyl portion contains 1 or 2 carbon atoms, such as benzyl, and wherein X is hydrogen, alkyl, alkoxy or halogen such as chlorine, fluorine and bromine.

The products of general formula (I) in which A is the CH$_2$ group may be prepared by reducing the corresponding products of the general formula (I) in which A is the CO group.

Hydrazine in the presence of an alkali metal hydroxide such as, for instance, sodium hydroxide or a metallic hydride such as sodium, potassium or lithium borohydride, or aluminum and lithium hydride, or various complex hydrides such as that of sodium and of bis (methoxy-2 ethoxy) aluminum or also diborane may be used as reducing agents.

The products of general formula (I) wherein A represents the CO group and R the hydrogen atom may be prepared in two stages by the schematic below:

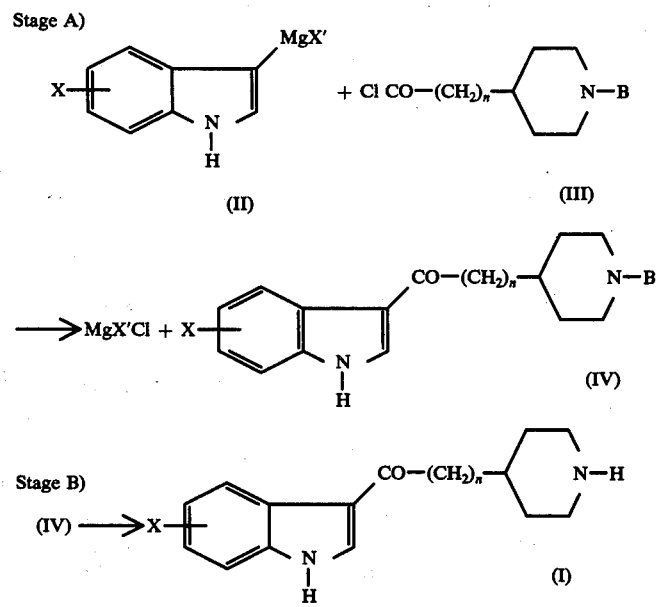

Stage A

Grignard's reagent of formula (II) wherein X is a halogen atom is obtained by reacting an alkylmagnesium halide such as methylmagnesium iodide with the corresponding indole. The reaction is generally conducted in an ether solvent such as diethyl ether, and usually at the boiling temperature of the solvent. The solution so obtained is then cooled to a temperature between 0° and 20° C and thereafter the acid chloride of formula (III) in an inert solvent such as benzene is added to the solution of II. The symbol B represents a group protecting the amine function of piperidine such as described by R. A. Boissonnas in Advances in Organic Chemistry 3, p 159, Interscience, 1963. An example of a protecting group is, for instance, a benzyloxycarbonyl group. The entire disclosure of Boissonnas is relied on herein and examples of the protecting group included there are incorporated herein by reference.

Stage B

Cleavage of the protective group B may be achieved under various conditions, depending on the nature of B (see Boissonnas). For example, the cleavage of the benzyloxycarbonyl group may be carried out by using an acid in an inert solvent such as acetic acid in ethanol or by controlled catalytic hydrogenation or by sodium in liquid ammonia.

The products of general formula (I) where A is the —CO— group and R an alkyl or aralkyl group may be prepared by alkylating or aralkylating products of formula (IV); the substituted N derivatives of (IV) thus obtained may then be subjected to the conditions described above to permit cleavage of the B protective group.

Methods known in the art may be used in the alkylation or aralkylation of the products of formula (IV) to place substituents on the N atom of the indole ring. Representative methods are described by W. J. Houlihan, INDOLES, part 1, page 90, Wiley, Interscience, 1972, which is relied on herein for this purpose and the disclosure incorporated by reference.

In order to eliminate secondary reactions with respect to the carbonyl group of the molecule, preferably excessively powerful metallation agents such as hydrides or the amides of alkali metals will not be used. Preferably conventional alkylation or aralkylation agents such as the alkyl or aralkyl halides in the presence of a base such as potassium carbonate in an inert solvent such as acetone will be used.

The products obtained by this procedure may be purified by suitable physical methods such as distillation, crystallization, chromatography and the like. Appropriate chemical methods may also be used such as salt formation, base regeneration and the like. The compounds obtained thereby may be transformed into addition salts by the action of mineral or organic acids in an appropriate solvent.

The examples set forth below are illustrative of the invention:

EXAMPLE 1: INDOLYL-3 (PIPERIDYL-4 METHYL) KETONE

An iodine crystal is added to a suspension of 7.1 gm of magnesium turnings in 90 ml of anhydrous ether. This is followed by heating under reflux and slow addition of a solution of 42 gm of methyl iodide in 90 ml of anhydrous ether. Refluxing is maintained until the magnesium disappears. The resulting solution is cooled to 20° C. There is then added to this solution, 15.7 gm of a solution of indole in 90 ml of anhydrous ether. The addition takes place over a period of 10 minutes. The ensuing exothermic reaction brings the ether solution to the refluxing temperature and refluxing conditions are maintained by heating for 1 hour. The solution obtained in this manner is then cooled to a temperature between 0 and 5° C. To this solution there is then gradually added a benzene solution of the chloride of benzyloxycarbonyl -1 piperidyl-4 acetic acid. The latter is obtained by reacting 31.8 gm of thionyl chloride with 37.1 gm of benzyloxycarbonyl-1 piperidyl-4 acetic acid in accordance with the procedure shown in I. de Graw, J. Heterochem. 3, 90, 1966. As a result of the reaction with the acid chloride, the oily product salts out and then crystallizes. The suspension is shaken for 15 hours at ambient temperature. Then 30 ml of an aqueous solution of 2 N hydrochloric acid are added. Dissolution takes place at once.

The organic phase is decanted, dried on magnesium sulfate and then evaporated. The residual oil (54.3 gm) is dissolved in 500 ml of a 5 N solution of anhydrous hydrochloric acid in ethanol. The solution so obtained is heated under reflux for two hours, and then evaporated under partial vacuum. The residue is dissolved in 200 ml of boiling isopropanol and the solution is cooled to 0° C.

The crystals that appeared are centrifuged, dried and recrystallized in methanol. By this procedure, there is obtained 20 gm of indolyl-3 (piperidyl-4 methyl) ketone hydrochloride melting at a temperature above 280° C.

| | $C_{15}H_{18}N_2O \cdot HCl$ analysis | | |
|---|---|---|---|
| | C | H | N |
| computed | 64.6 | 6.82 | 10.06 |
| measured | 64.59 | 6.80 | 9.84 |

The products below are prepared in a similar manner:

EXAMPLE 2: (METHOXY-5 INDOLYL-3) (PIPERIDYL-4 METHYL) KETONE

As starting materials there may be employed methoxy-5 indole and benzyloxycarbonyl-1 piperidyl-4 acetic acid, and by using the same procedure as set forth above there is obtained (methoxy-5 idolyl-3) (piperidyl-4 methyl) ketone hydrochloride, melting at 265° C.

| | $C_{16}H_{20}N_2O_2 \cdot HCl$ analysis | | |
|---|---|---|---|
| | C | H | N |
| computed | 62.2 | 6.81 | 9.09 |
| measured | 62.3 | 6.85 | 8.98 |

EXAMPLE 3: (CHLORO-5 INDOLYL-3) (PIPERIDYL-4 METHYL) KETONE

By following the procedure as set forth in example 1 and using as starting materials chloro-5 indole and benzyloxycarbonyl-1 piperidyl-4 acetic acid, there may be obtained (chloro-5 indolyl-3) (piperidyl-4 methyl) ketone hydrochloride. The product melting above 260° C.

| | $C_{15}H_{17}ClN_2O \cdot HCl$ | | | |
|---|---|---|---|---|
| | C | H | N | Cl |
| computed | 57.5 | 5.75 | 8.94 | 22.7 |
| measured | 57.53 | 5.62 | 8.93 | 22.35 |

EXAMPLE 4: (INDOLYL-3)-1 (PIPERIDYL-4)-3 PROPANONE

The compound (indolyl-3) (piperidyl-4)-3 propanone methane sulfate, melting at 198° C is obtained by following the same procedure as set forth in example 1 using instead as starting materials the compounds indole and benzyloxycarbonyl-1 piperidyl-4 proprionic acid.

| | $C_{16}H_{20}N_2O \cdot CH_4O_3S$ analysis | | | |
|---|---|---|---|---|
| | C | H | N | S |
| computed | 58 | 6.82 | 7.95 | 9.1 |
| measured | 58.1 | 7.03 | 7.78 | 8.94 |

EXAMPLE 5: INDOLYL-3 PIPERIDYL-4 KETONE

Employing indole and benzyloxycarbonyl-1 piperidyl-4 carboxylic acid as the starting material and by following the procedure of example 1 there may be obtained the product indolyl-3 piperidyl-4 ketone hydrochloride which has a melting point of 260° C.

| | $C_{14}H_{16}N_2O \cdot HCl$ analysis | | |
|---|---|---|---|
| | C | H | N |
| computed | 63.4 | 6.42 | 10.59 |
| measured | 63.5 | 6.46 | 10.56 |

EXAMPLE 6: (METHYL-1 INDOLYL-3) (PIPERIDYL-4 METHYL) KETONE

A suspension of 2 gm of anhydrous potassium carbonate in a solution of 0.6 gm of indolyl-3 (benzyloxycarbonyl-1 piperidyl-4 methyl) ketone and 1 gm of methyl iodide is refluxed for 6 hours. Following cooling to ambient temperature, the potassium carbonate removed by centrifuging and the filtrate obtained thereby is evaporated under partial vacuum. The oily residue obtained is dissolved in 5 ml of a solution of 5 N anhydrous hydrochloric acid in ethanol and the solution thus obtained is heated at reflux conditions for one hour. The ethanol is evaporated under partial vacuum and the residue is recrystallized in ethanol. The product obtained by this procedure is 0.28 gm of (methyl-1 indolyl-3) (piperidyl-4 methyl) ketone hydrochloride with a melting point at 272° C.

NMR* SPECTRUM $(CDCL_3—CF_3COOH)\delta$: 8.2 – 7.3 ppm (aromatics) 3.6 – 2.8 ppm ($—NCH_2—$ and $—CO—CH_2$). 3.8 ppm ($N—CH_3$) – 1.6-2.2 ppm (CH and $CH_2$).

EXAMPLE 7: (BENZYL-1 INDOLYL-3) (PIPERIDYL-4 METHYL) KETONE

Following the same procedure as in example 6 but instead starting with the compounds indolyl-3(benzyloxycarbonyl-1 piperidyl-4 methyl) ketone and benzyl bromide, there is obtained (benzyl-1 indolyl-3) (piperidyl-4 methyl) ketone hydrochloride. The product has a melting point of 152° C.

NMR SPECTRUM $(CDCl_3 — CF_3COOH)\delta$: 8.2-7.3 ppm (aromatics) 7.6 ppm (NH) . 5.4 ppm ($—CH_2—C_6H_5$) . 3.6 – 3 ppm ($N—CH_2$ and $COCH_2$) - 1.7 – 2.2 ppm (CH— and $CH_2$)

EXAMPLE 8: [(METHOXY-5 INDOLYL-3)-2 ETHYL]-PIPERIDINE

A solution of 0.54 gm of (methoxy-5 indolyl-3) (piperidyl-4 methyl) ketone in 4 ml of tetrahydrofuran is added to a suspension of 0.152 gm of aluminum hydride and lithium hydride in 8 ml of anhydrous tetrahydrofuran in an atmosphere of nitrogen. The mixture is heated with reflux for 4 hours, and then cooled to 0° C. Thereupon, there is added to the cooled mixture in a sequential manner, 0.15 ml of water, 0.12 ml of an aqueous solution of 5 N sodium hydroxide and 0.6 ml of water. The mineral salts formed are separated by centrifuging and then washed twice with a total of 20 ml of methylene chloride.

The collected solutions are dried using potassium carbonate and then evaporated under partial vacuum. The product obtained is 0.3 gm of an oil which crystallizes in ethyl acetate. The resulting compound is [(methoxy-5 indolyl-3)-2 ethyl]-4 piperidine, which has a melting point of 114° C.

NMR SPECTRUM $(CDCl_3)\delta$: 6.8–7.2 ppm (aromatics). 3.8 ppm ($CH_3O$). 2.3 ppm ($N—CH_2$; $\pi$ $CH_2$). 1-2 ppm (CH and $CH_2$).

EXAMPLE 9: [(METHYL-1 INDOLYL-3)-2 ETHYL]-4 PIPERIDINE 0.5 gm of bis(methoxy-2 ethoxy) sodium aluminum hydride in a 70% solution in toluene is added to a solution of 0.29 gm of (methyl-1 indolyl-3) (piperidyl-4 methyl) ketone in 10 ml of toluene. The mixture is heated under refluxing conditions for 15 hours, and then cooled to 0° C. 10 ml of an aqueous solution of 5 N sodium hydroxide is added dropwise thereto, followed by stirring for 1 hour. The organic phase is decanted, washed with water, dried using potassium carbonate and evaporated under partial vacuum. 0.26 gm of oil is obtained, which is purified by chromatography and hydrochloride formation. The product obtained is 0.1 gm of [(methyl-1 indolyl-3)-2 ethyl]-4 piperidine hydrochloride which has a melting point of 198° C.

| | $C_{16}H_{22}N_2 \cdot HCl$ analysis | | |
|---|---|---|---|
| | C | H | N |
| computed | 68.9 | 8.26 | 10.05 |
| measured | 68.69 | 8.10 | 9.97 |

In a similar manner, the following products are obtained:

EXAMPLE 10: [(INDOLYL-3)-2 ETHYL]-4 PIPERIDINE

The same procedure was used as in example 9 except that the compound indolyl-3 (piperidine-4 methyl) ketone is reduced. The product obtained thereby is [(indolyl-3)-2 ethyl] 4 piperidine. The hydrochloride thereof has a melting temperature of 167° C.

| | $C_{15}H_{20}N_2 \cdot HCl$ analysis | | |
|---|---|---|---|
| | C | H | N |
| computed | 68.05 | 7.94 | 10.6 |

-continued

| $C_{15}H_{20}N_2 \cdot HCl$ analysis | | | |
|---|---|---|---|
| | C | H | N |
| measured | 68.4 | 8.32 | 10.7 |

EXAMPLE 11: (INDOLYL-3 METHYL) -4 PIPERIDINE

The same procedure is used in example 9 except that the compound indolyl-3 piperidyl-4 ketone is reduced. The product obtained is (indolyl-3 methyl)-4 piperidine which has a melting point of 172° C.

| $C_{14}H_{18}N_2$ analysis | | | |
|---|---|---|---|
| | C | H | N |
| computed | 78.5 | 8.61 | 13.09 |
| measured | 78.40 | 8.45 | 12.56 |

EXAMPLE 12: [(CHLORO-5 INDOLYL-3) -2 ETHYL] -4 PIPERIDINE

The same procedure is used in example 9 except that the compound (chloro-5 indolyl-3) (piperidyl-4 methyl) ketone is reduced. The product obtained thereby is [(chloro-5 indolyl-3) -2 ethyl] -4 piperidine, melting at 160° C.

| $C_{15}H_{19}ClN_2$ analysis | | | |
|---|---|---|---|
| | C | H | N |
| computed | 68.6 | 7.24 | 10.68 |
| measured | 68.65 | 7.31 | 10.57 |

EXAMPLE 13: [(INDOLYL-3)-3 PROPYL]-4 PIPERIDINE

The same procedure is used as in example 9 except that the compound (indolyl-3)-1 (piperidyl-4)-3 propanone is reduced. The product obtained is [(Indolyl-3 propyl]-4 piperidine in the form of oil. The fumaric acid salt thereof was found to melt at 228° C.

Anhydrotitrometric
Dosage: 100%
NMR SPECTRUM (CDCl$_3$): δ–7.5–7–6.7 (aromatics)
2.4–3.1. (N—CH$_2$), ≧ —CH$_2$),
1–2 ppm (CH and CH$_2$).

EXAMPLE 14: [(BENZYL-1 INDOLYL-3)-2 ETHYL]-4 PIPERIDINE

The same procedure is used as in example 9 except that the compound (benzyl-1 indolyl-3) (piperidyl-4 methyl ketone is reduced. The product obtained thereby is [(benzyl-1 indolyl-3)-2 ethyl]-4 piperidine in the form of non-crystallizing oil.

NMR SPECTRUM
(CDCl$_3$CF$_3$COOH)δ: 5.2 ppm (CH$_2$—C$_6$H$_5$)
8.2–7.3 ppm (aromatic)
3–3.6 ppm 9N—CH$_2$)
1.7–2.2 ppm (CH and CH$_2$)

PHARMACOLOGICAL PROPERTIES

The activity of the products of the invention was demonstrated by an inhibition test, in vitro, regarding the cerebral monoamine uptake by rat-brain synaptosomes by the method of Kannengiesser et al (Biochem. Pharmacol. 22, 73, 1973). The entire disclosure of Kannengiesser et al is relied on in this connection and incorporated herein by reference.

The results listed in the table below show that the products of the invention are characterized by selective action on cerebral serotonin, and that their activity of the other mediators (noradrevaline and dopamine) is from 20 to 3,000 times weaker. In particular, the products of examples 1, 9, 10 and 13 act more selectively than clomipramine.

DOSES INHIBITING 50% OF RECAPTURE BY BRAIN-RATE SYNAPTOSOMES OF NORADRENALINE (NA), OF DOPAMINE (DA) AND OF SEROTONIN (5HT).

| | $I_{50}(\mu M/L)$ | | |
|---|---|---|---|
| Products | NA | DA | 5HT |
| Example 1 | 20 | 65 | 0.08 |
| Example 2 | 160 | 70 | 0.65 |
| Example 3 | 30 | 12 | 0.60 |
| Example 9 | 60 | 60 | 0.02 |
| Example 10 | 8 | 4 | 0.04 |
| Example 11 | 5 | 4 | 0.15 |
| Example 13 | 13 | 5.5 | 0.04 |
| Clomipramine | 7 | 5 | 0.07 |

The effectiveness of the compounds of the present invention in blocking serotonine uptake also was shown using the potentiation test of 5-hydroxy tryptophane (5-HTP).

The products of the invention possess the significant property of potentiating the effects of 5-HTP which is the precursor agent of serotonin. This property was demonstrated in the male mouse CD$_1$ (Charles River) using the technique of Buus Lassens, J. Acta Pharmacol. 31, suppl. 1, 11–1972. This test consists of looking for the potentiation of the hypermotility induced by 5-HTP. for high dosages the precursor will induce very characteristic hypermotility with jumps. Now, the inhibotors of serotonin capture are capable of inducing the same behavior in the mouse previously treated with a low inactive dose of 5-HTP.

The animals are divided into groups of 25 mice and treated i.p. with 150 mg/kg of 5-HTP. The products to be tested are administered sub-cutaneously, 30 minutes after the 5-HTP, the control group receiving only the administrative vehicle. The overall motility of the animals is measured from the 45th to the 75th minute after (administration of) the 5-HTP. The results for the treated groups are shown in % increase in motility with respect to the control group. The table below shows the results obtained with three compounds.

| | Potentiation of 5-HTP Hypermotility in Mice | |
|---|---|---|
| Products | S.C. Doses in mg/kg | % Change With Respect to Controls |
| Example 10 | 5 | +196 |
| | 25 | +262 |
| Example 11 | 5 | − 12 |
| | 25 | + 25 |
| Example 9 | 5 | +134 |
| | 25 | +296 |
| Clomipramine | 15 | +190 |

This activity agrees well with the strong inhibiting effects noted for serotonin uptake, in vitro, for rat synaptosomes.

TOXICOLOGICAL PROPERTIES

The toxicity and acute symptomatologies of the compounds of the invention were determined in the male mouse $CD_1$ (Charles River) in intravenous and oral manner. The $LD_{50}$ were computed following three days' observation by the cumulative method of Reed & Muench (Am. J. Hyg. 27, 493, 1938).

The $LD_{50}$ that were obtained are shown in the table below:

| Products | Acute Toxicity In Mice $LD_{50}$ (mg/kg) | |
|---|---|---|
| | I.V. | Orally |
| Example 1 | 47 | between 300 and 900 |
| Example 2 | 44 | exceeds 900 |
| Example 3 | — | between 300 and 900 |
| Example 9 | 44 | 225 |
| Example 10 | 60 | 600 |
| Example 11 | 57 | 225 |
| Clomipramine | 45 | 380 |

These substances therefore behave indicating they are of low toxicity in mice.

THERAPEUTIC APPLICATIONS

The compounds of the invention and their pharmaceutically acceptable salts may be used in mammalian, including but not limited to human, therapy in the form of pills, tablets, lozenges, troches, capsules, suppositories, injectable or ingestable solutions and the like in the treatment of pathological conditions in mammals caused by disturbances in the functioning of the serotonin systems, in particular as regards the various psychological difficulties involving depression.

The mammals which may be treated, within the contemplation, include humans, as well as laboratory animals, for example, dogs, cats, guinea pigs, mice and rats.

For the foregoing purposes the compounds described above may be administered in a therapeutically effective amount, such as to a mammal, orally or parenterally.

For purposes of injection the compounds described above can be prepared in the form of solutions, suspensions or emulsions in vehicles conventionally employed for this purpose.

The dosage depends on the effects sought and on the manner of administration. Orally, for instance, it may range from 5 to 250 mg of active substance a day, each unit dose ranging from 1 to 50 mg per kg of body weight.

Appropriate pharmaceutically acceptable carriers, diluents and adjuvants may be and together with the compounds described herein in order to prepare the desired compositions for use in the treatment of pathological conditions in mammals.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host. While intravenous injection is a very effective form of administration, other modes can be employed.

We claim:

1. A method of treating a mammal afflicted with depression comprising administering to said mammal a therapeutically effective amount of a composition comprising a compound of the formula

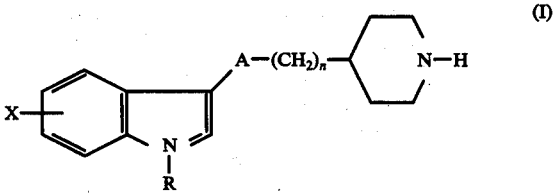

where R is hydrogen, an alkyl group having 1 to 4 carbon atoms or an aralkyl group of which the alkyl contains 1 or 2 carbon atoms; X is hydrogen, alkyl, alkoxy or alkylthio, the alkyl of each containing from 1 to 4 carbon atoms, or a halogen atom; A is —CO— or —$CH_2$—; and n is 1 to 2; and pharmaceutically acceptable salts thereof; in a pharmaceutically acceptable carrier therefor.

2. A method as defined in claim 1 wherein A is —CO—.

3. A method as defined in claim 1 wherein A is —$CH_2$—.

4. A method as defined in claim 1 wherein said compound is indolyl-3 (piperidyl-4 methyl) ketone.

5. A method as defined in claim 1 wherein said compound is (methoxy-5-indolyl-3) (piperidyl-4 methyl) ketone.

6. A method as defined in claim 1 wherein said compound is (chloro-5-indolyl-3) (piperidyl-4 methyl) ketone.

7. A method as defined in claim 1 wherein said compound is (indolyl-3)-1(piperidyl-4)-3 propanone.

8. A method as defined in claim 1 wherein said compound is indolyl-3 piperidyl-4 ketone.

9. A method as defined in claim 1 wherein said compound is (methyl-1 indolyl-3) (piperidyl-4 methyl) ketone.

10. A method as defined in claim 1 wherein said compound is (benzyl-1 indolyl-3) (piperidyl-4 methyl) ketone.

11. A method as defined in claim 1 wherein said compound is [(methoxy-5 indolyl-3)-2 ethyl]-piperidine.

12. A method as defined in claim 1 wherein said compound is [(methyl-1 indolyl-3)-2 ethyl]-4 -piperidine.

13. A method as defined in claim 1 wherein said compound is [(indolyl-3)-2 ethyl]-4 piperidine.

14. A method as defined in claim 1 wherein said compound is (indolyl-3 methyl)-4 piperidine.

15. A method as defined in claim 1 wherein said compound is [(chloro-5 indolyl-3)-2 ethyl]-4 piperidine.

16. A method as defined in claim 1 wherein said compound is [(indolyl-b 3)-3 propyl]-4 piperidine.

17. A method as defined in claim 1 wherein said compound is [(benzyl-1 indolyl-3)-2 ethyl]-4 piperidine.

18. A method as defined in claim 1 wherein the composition is administered in an amount equivalent to a dosage of from 1 to 50 mg per kg of body weight.

19. A composition for the treatment of a mammal afflicted with depression, comprising a compound selected from the group consisting of indolyl-3 (piperidyl-4 methyl) ketone;
(methoxy-5-indolyl-3) (piperidyl-4 methyl) ketone;
(chloro-5-indolyl-3) (piperidyl-4 methyl) ketone;
(indolyl-3)-1(piperidyl-4)-3 propanone;
indolyl-3 piperidyl-4 ketone;
(methyl-1 indolyl-3) (piperidyl-4 methyl) ketone;
(benzyl-1 indolyl-3) (piperidyl-4 methyl) ketone;
[(methoxy-5 indolyl-3)-2 ethyl]-piperidine;
[(methyl-1 -indolyl-3)-2 ethyl]-4 piperidine;
[(indolyl-3)-2 ethyl]-4 piperidine;
(indolyl-3 methyl)-4 piperidine;
[(chloro-5 indolyl-3)-2 ethyl]-4 piperidine;
[(indolyl-3)-3 propyl]-4 piperidine; and
[(benzyl-1 indolyl-3)-2 ethyl]-4 piperidine.

20. The composition of claim 19 wherein said compound is indolyl-3 (piperidyl-4 methyl) ketone.

21. The composition of claim 19 wherein said compound is (methoxy-5-indolyl-3) (piperidyl-4 methyl) ketone.

22. The composition of claim 19 wherein said compound is (chloro-5-indolyl-3) (piperidyl-4 methyl) ketone.

23. The composition of claim 19 wherein said compound is (indolyl-3)-1(piperidyl-4)-3 propanone.

24. The composition of claim 19 wherein said compound is indolyl-3 piperidyl-4 ketone.

25. The composition of claim 19 wherein said compound is (methyl-1 indolyl-3) (piperidyl-4 methyl) ketone.

26. The composition of claim 19 wherein said compound is (benzyl-1 indolyl-3) (piperidyl-4 methyl) ketone.

27. The composition of claim 19 wherein said compound is [(methoxy-5 indolyl-3)-2 ethyl)-piperidine.

28. The composition of claim 19 wherein said compound is [(methyl-1 indolyl-3)-2 ethyl]-4 piperidine.

29. The composition of claim 19 wherein said compound is [(indolyl-3)-2 ethyl]-4 piperidine.

30. The composition of claim 19 wherein said compound is (indolyl-3 methyl)-4 piperidine.

31. The composition of claim 19 wherein said compound is [(chloro-5 indolyl-3)-2 ethyl]-4 piperidine.

32. The composition of claim 19 wherein said compound is [(indolyl-3)-3 propyl]-4 piperidine.

33. The composition of claim 19 wherein said compound is [(benzyl-1 indolyl-3)-2 ethyl]-4 piperidine.

* * * * *

UNITED STATES PATENT OFFICE
CERTIFICATE OF CORRECTION

PATENT NO. : 4,064,255
DATED : December 20, 1977
INVENTOR(S) : Alain André CHAMPSEIX et al.

It is certified that error appears in the above-identified patent and that said Letters Patent are hereby corrected as shown below:

Col. 11, line 10, cancel from "19. A composition" to and including "piperidine." in col. 11, line 29, and insert the following claim:

19. A composition for the treatment of a mammal afflicted with depression, comprising a compound selected from the group consisting of indolyl-3(piperidyl-4 methyl) ketone;
    (methoxy-5-indolyl-3)(piperidyl-4 methyl) ketone;
    (chloro-5-indolyl-3)(piperidyl-4 methyl) ketone;
    (indolyl-3)-1(piperidyl-4)-3 propanone;
    indolyl-3 piperidyl-4 ketone;
    (methyl-1 indolyl-3)(piperidyl-4 methyl) ketone;
    (benzyl-1 indolyl-3)(piperidyl-4 methyl) ketone;
    [(methoxy-5 indolyl-3)-2 ethyl]-piperidine;
    [(methyl-1 indolyl-3)-2 ethyl]-4 piperidine;
    [(indolyl-3)-2 ethyl]-4 piperidine;
    (indolyl-3 methyl)-4 piperidine;
    [(chloro-5 indolyl-3)-2 ethyl]-4 piperidine;
    [(indolyl-3)-3 propyl]-4 piperidine; and
    [(benzyl-1 indolyl-3)-2 ethyl]-4 piperidine in an effective amount and a pharmaceutically acceptable carrier therefor.

Signed and Sealed this

Tenth Day of July 1979

[SEAL]

Attest:

*Attesting Officer*

LUTRELLE F. PARKER
*Acting Commissioner of Patents and Trademarks*